US010225086B2

(12) United States Patent
Benchetrit et al.

(10) Patent No.: US 10,225,086 B2
(45) Date of Patent: Mar. 5, 2019

(54) IMAGE FINGERPRINTING

(71) Applicant: KONINKLIJKE PHILIPS N.V., Eindhoven (NL)

(72) Inventors: Uri Benchetrit, Haifa (IL); Santosh Vidyullata Vijay, Bangalore (IN); Shlomo Gotman, Haifa (IL); Amiaz Altman, Tel Aviv (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 125 days.

(21) Appl. No.: 15/507,282

(22) PCT Filed: Sep. 2, 2015

(86) PCT No.: PCT/IB2015/056659
§ 371 (c)(1),
(2) Date: Feb. 28, 2017

(87) PCT Pub. No.: WO2016/035020
PCT Pub. Date: Mar. 10, 2016

(65) Prior Publication Data
US 2018/0241563 A1  Aug. 23, 2018

Related U.S. Application Data

(60) Provisional application No. 62/044,452, filed on Sep. 2, 2014.

(51) Int. Cl.
*H04L 9/32* (2006.01)
*G06F 19/00* (2018.01)
(Continued)

(52) U.S. Cl.
CPC ........ *H04L 9/3231* (2013.01); *G06F 17/3002* (2013.01); *G06F 17/30032* (2013.01);
(Continued)

(58) Field of Classification Search
CPC ........ G06F 17/30247; G06F 17/30256; G06F 17/30259; G06F 19/30; G16H 30/20;
(Continued)

(56) References Cited

U.S. PATENT DOCUMENTS

| 5,943,435 A | 8/1999 | Gaborski ............... 382/132 |
| 2004/0078299 A1 | 4/2004 | Down-Logan et al. |

(Continued)

FOREIGN PATENT DOCUMENTS

CN  103226582 A  7/2013

OTHER PUBLICATIONS

Stamm, et al., "Forensic detection of image manipulation using statistical intrinsic fingerprints", IEEE Transactions on Information Forensics and Security, vol. 5, No. 3, Sep. 1, 2010.
(Continued)

*Primary Examiner* — Andrew W Johns

(57) ABSTRACT

A computing system includes a memory (114) that stores instructions of an image finger printer module (116). The computing system further includes a processor (112) that receives a bitmap digital image and generates a first key, which is an electronic compressed representation of the bitmap digital image, that uniquely identifies the bitmap digital image. A computer readable storage medium is encoded with computer readable instructions, which, when executed by a processor, causes the processor to: normalize a bitmap digital medical image; sample the normalized bitmap digital medical image; post-processes the sampled, normalized bitmap digital medical image; package the post-processed, sampled, normalized bitmap digital medical image as a key that uniquely identifies the bitmap digital medical image.

21 Claims, 4 Drawing Sheets

(51) Int. Cl.
  *G06F 17/30* (2006.01)
  *G06K 9/00* (2006.01)
  *H04L 9/08* (2006.01)

(52) U.S. Cl.
  CPC ............ *G06F 19/00* (2013.01); *G06F 19/321* (2013.01); *G06K 9/00087* (2013.01); *H04L 9/0866* (2013.01)

(58) Field of Classification Search
  CPC ... H04L 9/0816; H04L 9/0861; H04L 9/3236; H04L 9/3242
  See application file for complete search history.

(56) References Cited

U.S. PATENT DOCUMENTS

| | | | |
|---|---|---|---|
| 2005/0129169 A1 | 6/2005 | Donnelly et al. | 378/5 |
| 2009/0240684 A1* | 9/2009 | Newell et al. .... G06F 17/30256 | 707/5 |
| 2010/0014755 A1 | 1/2010 | Wilson | 382/173 |
| 2010/0080426 A1 | 4/2010 | Schmitt et al. | 382/128 |
| 2010/0092084 A1* | 4/2010 | Perronnin et al. .... G06K 9/00442 | 382/170 |
| 2010/0098342 A1* | 4/2010 | Davis et al. ......... G06K 9/0063 | 382/220 |
| 2012/0237096 A1 | 9/2012 | Tobin et al. | 382/128 |
| 2013/0268407 A1 | 10/2013 | Boncyk et al. .... G06Q 30/0623 | |
| 2014/0029854 A1 | 1/2014 | Lyons et al. | 382/190 |
| 2014/0125822 A1 | 5/2014 | Mullins et al. .... H04N 1/00214 | |
| 2014/0129627 A1 | 5/2014 | Baldwin et al. ........ H04L 67/02 | |

OTHER PUBLICATIONS

Macura, et al., "Radiology image resource with a case-based retrieval system", Case-Based Reasoning Research and Development, vol. 1010 of the series Lecture Notes in Computer Science, Abstract 1995.

Petrakis, et al., "Similarity Searching in Medical Image DataBases", IEEE Transactions on Knowledge and Data Enginnering. vol. 9, No. 3, May/Jun. 1197, pp. 435-447.

* cited by examiner

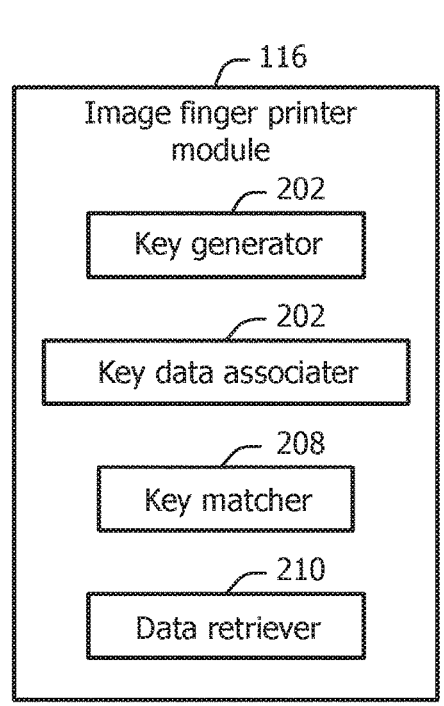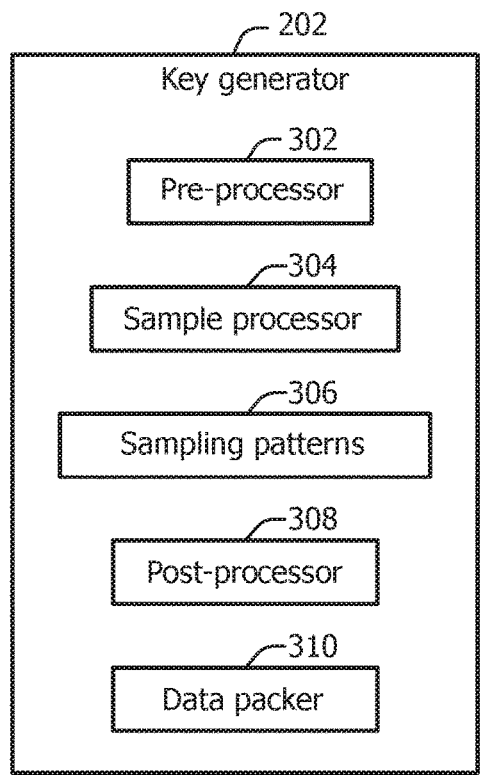
FIG. 2
FIG. 3
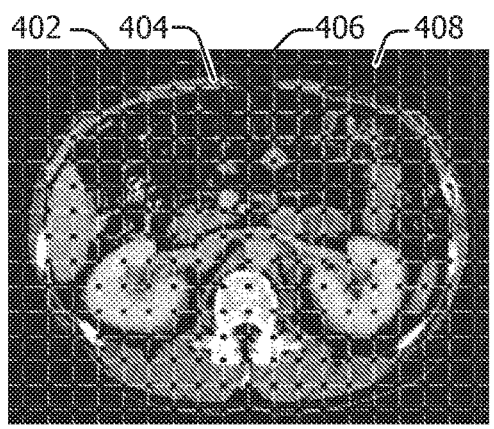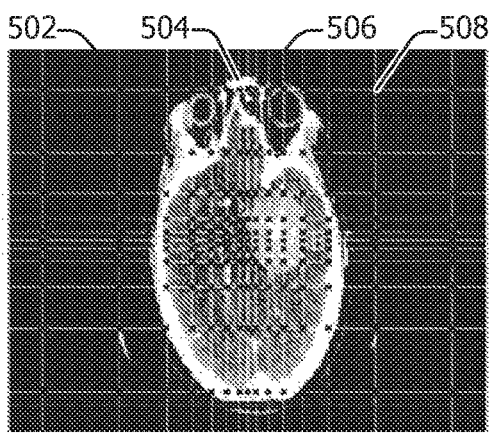
FIG. 4
FIG. 5

IMAGE FINGERPRINTING

CROSS REFERENCE TO RELATED APPLICATIONS

This application is the U.S. National Phase application under 35 U.S.C. § 371 of International Application No. PCT/IB2015/056659, filed Sep. 2, 2015, published as WO 2016/035020 on Mar. 10, 2016, which claims the benefit of U.S. Provisional Patent Application No. 62/044,452 filed Sep. 2, 2014. These applications are hereby incorporated by reference herein.

The following generally relates to image processing and more particularly to uniquely identifying digital bitmap images, and is described with particular application to imaging modalities such as computed tomography (CT), positron emission tomography (PET), single photon emission computer tomography (SPECT), magnetic resonance imaging (MRI), X-ray, ultrasound (US), etc. for medical and/or non-medical (e.g., non-destructive testing) applications, and is also amenable to other imaging modalities and/or applications.

A digital image, generally, is a numeric representation of a two-dimensional image. Examples of digital images include vector images and raster images. A vector image is an image generated through mathematical calculations (e.g., using geometrical primitives such as points, lines, curves, polygons, etc.) from one point to another (a vector) that form geometrical shapes. Vector images are scalable without loss of resolution. However, modern displays and printers are raster devices, and vector formats are converted to raster format before they are displayed or printed.

Raster images (or bitmaps) have a finite set of digital values referred to as pixels and contain a fixed number of rows and columns of pixels. Each pixel is a quantized value that represents a brightness of a given color at any specific point. For grayscale images, each pixel is typically represented by 256 possible gray intensity values (one byte). For color images, each pixel is typically represented by three values, r, g and b. The values indicate the color intensity of red, green, and blue, respectively, needed to render the pixel on screen. The range of intensities is the same as grayscale images; a value of 0 indicates none of the color appears in the pixel, and a value of 255 indicates the highest level of the color is evident in the pixel.

Digital images have been labeled with identification information. Examples of such labeling have included visible annotations (e.g., descriptive labels overlaid on top of the image), visible barcodes (e.g., one or two-dimensional bar codes), visible and invisible digital watermarks, invisible metadata, and any combination of these labels. Such information can be extracted from a digital image and used to identify the digital image. Unfortunately, in the case of an unlabeled digital image, such information does not exist and cannot be extracted to identify the digital image.

Aspects described herein address the above-referenced problems and others.

The following describes an approach to create a fingerprint for a digital bitmap image that uniquely identifies the image, without any labelling of the digital bitmap image. In general, the fingerprint is an electronically formatted key that is a compressed summary of the digital bitmap image. The fingerprint can then be searched in a database that has been indexed using the same fingerprinting scheme. A non-indexed database may be searched using ad-hoc on the fly fingerprinting.

In one aspect, a method includes receiving, from a client device, a digital image being visually observed and a first request, in electronic format, for electronically formatted first data associated with the digital image. The method further includes generating a first key for the digital image, wherein the first key uniquely identifies the digital image. The method further includes comparing the first key with previously or on the fly generated keys for images stored in an image database, wherein the previously or on the fly generated keys uniquely identify the images. The method further includes identifying a second key of the previously or on the fly generated keys that exactly matches the first key, within a predetermined tolerance. The method further includes retrieving a first value paired with the second key, in response to the exact match. The method further includes retrieving the first data associated with the digital image based on the first value. The method further includes returning, to the client device, the retrieved first data.

In another aspect, a computing system includes a memory that stores instructions of an image finger printer module. The computing system further includes a processor that receives a bitmap digital image and generates a first key, which is an electronic compressed representation of the bitmap digital image, that uniquely identifies the bitmap digital image.

In another aspect, a computer readable storage medium is encoded with computer readable instructions. The computer readable instructions, when executed by a processor, causes the processor to: normalize a bitmap digital medical image; sample the normalized bitmap digital medical image; post-processes the sampled, normalized bitmap digital medical image; package the post-processed, sampled, normalized bitmap digital medical image as a key that uniquely identifies the bitmap digital medical image.

The invention may take form in various components and arrangements of components, and in various steps and arrangements of steps. The drawings are only for purposes of illustrating the preferred embodiments and are not to be construed as limiting the invention.

FIG. 1 schematically illustrates a computing system with an image finger printer module in connection with at least one client, one or more image databases, one or more associated data databases, one or more look-up table (LUT) databases.

FIG. 2 schematically illustrates an example of the image finger printer module.

FIG. 3 schematically illustrates an example of a key generator of the image finger printer module.

FIG. 4 illustrates an example sampling pattern.

FIG. 5 illustrates another example sampling pattern.

Figure 1:
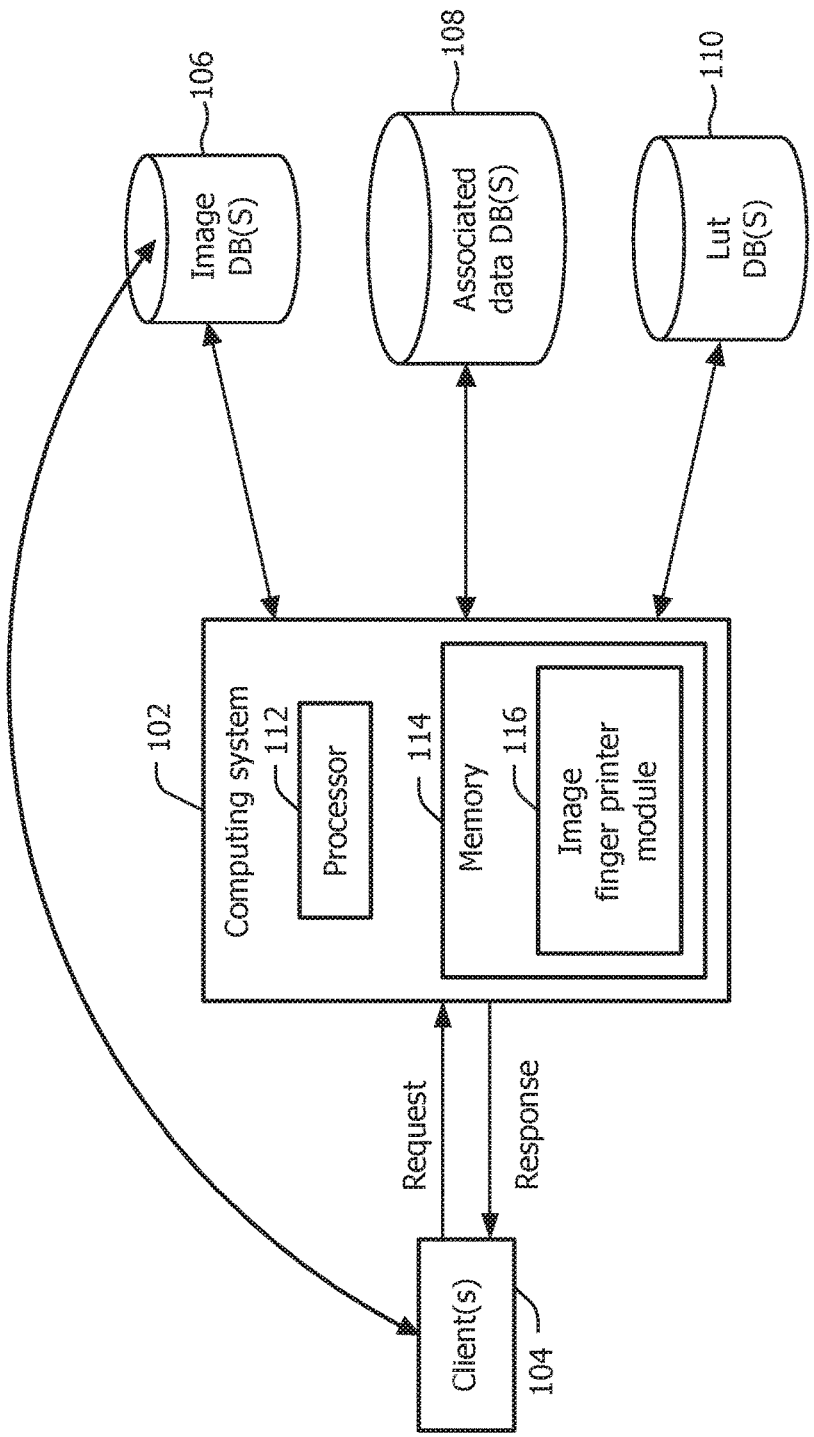

FIG. 1 schematically illustrates a computing system 102 in connection with at least one client 104, one or more image databases 106, one or more associated data databases 108, one or more look-up table (LUT) databases 110.

The one or more image databases 106 stores images such as CT, PET, SPECT, MRI, X-ray, US, etc. images. Such images at least include bitmap digital images. The one or more image databases 106 may be located within a single physical entity or distributed across physical entities, in cloud-based storage, part of a same or shared across different healthcare networks, located at a same or different geographical location, accessed through a direct link or over a network, etc. Examples also include a picture archiving and communication system (PACS), a radiology information system (RIS), a hospital information system (HIS), an electronic medical record (EMR), etc.

The one or more associated data databases 108 stores information associated with one or more of the images stored in the one or more image databases 106. Examples of such data include patient history, laboratory results, a processed version of the image, data to embed in an image, a computer executable application, etc. The one or more associated data databases 108, likewise, may be located within a single physical entity or distributed across physical entities, cloud based, part of a same or shared across different healthcare network, located at a same or different geographical location, accessed through a direct link or over a network, etc., and examples likewise include a PACS, a RIS, a HIS, an EMR, etc.

The one or more look-up table databases 110 stores links between the images stored in the one or more image databases 106 and the associated data stored in the one or more non-image databases 108. A link, in one instance, includes a key/value pair. The key identifies the image and the value is an address to a location of data associated with the image and/or the actual associated data. As described in greater detail below, the key is an electronic compressed representation of the bitmap digital image that provides a unique identification for the digital image. The one or more look-up table databases 110 may be likewise located and/or accessed.

The client 104 can retrieve and view images from and/or store images in the one or more image databases 106. In one instance, the client 104 transmits, in electronic format, a request to the computing system 102 for data from at least one of the one or more image databases 106, the one or more associated databases 108, and/or the one or more look-up table databases 110 corresponding to an image of interest. In another instance, the client 104 transmits, in electronic format, a request to the computing system 102 to add data to at least one of the one or more image databases 106, the one or more associated databases 108, and/or the one or more look-up table databases 110. The client 104 can be a computer based system such as a as PACS, an imaging system, a smartphone, a web-based application, etc.

The computing system 102 includes at least one processor 112 (e.g., a microprocessor, a central processing unit (CPU), a controller, etc.) that executes at least one computer readable instruction stored in computer readable storage medium ("memory") 114, which excludes transitory medium and includes physical memory and/or other non-transitory medium. The microprocessor 112 may also execute one or more computer readable instructions carried by a carrier wave, a signal or other transitory medium. The computing system 102 may include one or more input devices (e.g., a mouse, a keyboard, etc.) and/or one or more output devices (e.g., a display monitor, a filmer, etc.)

In the illustrated embodiment, the computing system 102 and the client 104 are separate devices. In a variation, the computing system 102 and the client 104 are part of a same device. In yet another instance, the image finger printer module 116 is installed on both the computing system 102 and the client 104. In addition, the computing system 102 can be located in a same or different location as the client 104. Furthermore, the computing system 102 can be managed by the same or different entity as the client 104. For example, in one instance, the computing system 102 and the client 104 belong to a same medical facility. In a variation, the computing system 102 is part of a third party service, which can be subscription or otherwise based, free or fee based, including use based fees and/or flat fee recurring fees.

The instruction, in this example, includes an image finger printer module 116. The image finger printer module 116 fingerprints (i.e., generates keys for) images. As described in greater detail below, in one instance, generating a key for a bitmap digital image includes sampling the bitmap digital image based on a predetermined sampling pattern and generating the key based on the samples, and not the entire bitmap digital image. The key uniquely identifies the bitmap digital image. As further described below, the image finger printer module 116 can link the key with associated data and store a key/value pair in the look-up table database(s) 110 and/or employ the key to retrieve data associated with the image.

For example, a key can be used with two incompatible applications such as a "closed" legacy application that allows fetching an image from the image database 106 and displaying it on a monitor, and an "open" newer application that allows farther manipulation on an image, when there is a need to manipulate on the newer application the same image that is displayed on the legacy application, and these two applications cannot exchange information directly. One example includes a legacy application that does not support spectral images. In this instance, the key allows the legacy application to retrieve spectral data processed with a different application by identifying the displayed image with the key and then retrieving spectral associated with the image.

In another instance, fingerprinting images may help with keeping the integrity of databases. As an example, ad-hoc fingerprinting may help when looking for duplicated images on one or more databases. In this case, all the images may be fingerprinted and then the fingerprints may be searched for duplications. In a deterministic process, similar images generate similar fingerprints. Therefore, when similar fingerprints are identified, corresponding images are identified as duplicates. Another example is making sure that one database (target), serving for instance as a backup or a sync database, includes at least a copy of all the images found on another database (source). Here again, all the images may be fingerprinted and then the fingerprints may be analyzed accordingly to verify the required level of data integrity.

Data can be transferred between the computing system 102 and the client 104 and the databases 106, 108 and/or 110 through Digital Imaging and Communications in Medicine (DICOM), Health Level 7 (HL7), and/or other protocols. The computing system 102 can be a third party pay or free service, part of an imaging system, a dedicated computing system external and remote from an imaging system, etc.

FIG. 2 schematically illustrates an example of image finger printer module 116. The image finger printer module 116 includes a key generator 202 that generates a key for an input bitmap digital image. Briefly turning to FIG. 3, an example of the key generator 202 is illustrated.

The key generator 202 includes a pre-processor 302. The pre-processor 302 normalizes the bitmap digital image, if needed. In one instance, the pre-processing ensures that the sampled data will be indexed as intended. For example, in one instance, the normalization ensures that the sampled data will be at the correct locations on the image as it will be rendered on a display when it is entirely presented using a basic projection (e.g., no zoom, pan, rotate, etc.). In a variation, the pre-processor 302 is omitted.

The key generator 202 further includes a sample processor 304. The sample processor 304 samples the normalized bitmap digital image. The sample processor 304 samples the normalized bitmap digital image based on a sampling pattern from the sampling patterns 306. The sampling pattern provides a reduction in dimensionality by sampling a sub-set of the pixels of the normalized bitmap digital image. The sampling pattern identifies which pixels will be sampled and in what order.

By way of non-limiting example, the normalized bitmap digital image is a two-dimensional digital image with a fixed number of rows and columns (N×M pixels). Each pixel $P_{i,j}$ at coordinate {i, j} has a quantized value of D bits that represent the color or greyscale at any specific point of the image. The sampling pattern represents an ordered collection SP of pixel coordinates from which the pixel data will be extracted.

The sampling pattern may be as simple as a uniformly spaced regular grid, or one that is based on geometrical significance of some areas of the normalized bitmap digital image. For instance, in radiology, the sample pattern may sample more pixel data close to the center of the normalized bitmap digital image and less from the outer parts that are normally uniformly dark. FIGS. 4 and 5 illustrate two non-limiting examples of sampling patterns overlaid over two different bitmap digital image.

FIG. 4 shows an image 402 including an axial slice 404 through the abdomen. The illustrated sampling pattern includes a uniformly spaced regular grid 406 (shown as horizontal and vertical lines). With this example, a sample is extracted at each row/column intersection 408 of the grid 406, which is the point at which the horizontal and vertical lines coincide with a pixel. In a variation, the sample is extracted at a predetermined offset or shift from each row/column intersection 408 of the grid 406.

FIG. 5 shows an image 502 including an axial slice 504 through the head. The illustrated sampling pattern is more dense at a central region of the image 502 and becomes less dense in a direction from the central region to peripheral regions of the image 502. Likewise, a sample is extracted at each row/column intersection 508 of the grid 506, and, in a variation, the sample is extracted at a predetermined offset or shift from each row/column intersection 508 of the grid 506.

The sampling patterns of FIGS. 4 and 5 are provided for explanatory purposes and are not limiting. For example, in a variation, the sample pattern is a function G, which maps an index k of the element in the sampled vector into a pixel coordinate $P_{i,j}$ of the input two-dimensional digital image. Such patterns may include the intersection of radial rays (sourced from a given focal point on the image) with concentric circles with varying diameters, varying pitch of a spiral, etc. In addition, suitable patterns may include different areas of spares and dense sampling. Increasing the sampling may increase the probability of key uniqueness. Less sampling consumes less time and memory.

The sampling pattern for a particular image is selected such that resulting key is unique to that image and reproducible. As such, the particular pattern may be based on the image modality, the scanned anatomy, etc. Furthermore, the same sampling pattern used to generate keys for images in the one or more image database(s) 106 is also used to generate a key for an input image. This guarantees an exact match between the key for the input image and a key for the same image in the one or more image database(s) 106. An exact match herein may include a tolerance to accommodate any artifact in the key generating process. In this case, a match within the tolerance is considered an exact match.

It is to be appreciated that more than one key can be generated for a bitmap digital image. In this instance, different sampling patterns can be used to generate the difference keys. When matching a currently displayed bitmap digital, at least one of the sampling patterns must be known and used to generate the key for the currently displayed bitmap digital. Where more than one of the patterns is known, multiple keys can be generated for the currently displayed bitmap digital. A single one or more a plurality of the multiple keys can then be matched to the keys for the bitmap digital in the one or more image database(s) 106.

Returning to FIG. 3, the key generator 202 includes a post-processor 308. The post-processor 308 processes the samples. At this stage, each sample is a copy of an associated pixel and can be equal to the ordered collection of the sampled data without any farther processing. The sampling pattern convention dictates the order of the elements in the fingerprint. The post-processor 308 farther manipulates the sampled data, for example, to provide uniqueness, robustness, and/or compactness.

By way of example, the input image may have been manipulated through a window/level setting. For this, a look-up-table (LUT) is used to map between a range of CT Numbers (i.e., Hounsfield Units, or HU) into rendered grayscale pixel values. For instance, setting a narrow window of CT Numbers will improve the low-contrast discrimination in the displayed image. Since different "window level setting" generate different images with different pixel color (or gray) intensity values, different fingerprints would be generated for a same image unless the window level setting is accounted for.

The window/level setting has been applied as an affine linear transformation. With such a transform, it is possible to transform each of the sampled data elements using a function T prior to including it in a final fingerprint. Such function may include partitioning the range of the pixels' quantized values of D bits into several discrete ranges R. For instance, for a pixel that is represented by 8 bits (D=8) the range of quantized values for a pixel is 0 to 255. A function T may split this range into two equal ranges.

For pixel data in the lower range of zero (0) to 127, function T will return zero (0) and for the higher range of 128 to 255, function T will return one (1). Then the fingerprint will be composed of a combination of only values zero (0) and one (1). This means function T transformed the sampled pixels from greyscale (or color) into black and white. Other schemes are also contemplated herein. In a variation, the post-processor 308 is omitted.

The key generator 202 further includes a data packer 310. The data packer 310 packages the post-processed samples, creating the key. The key may include optional metadata that identifies the pre-processing, the sampling patter, and/or the post-processing. In one instance, a length of a key (excluding the metadata) is L bits and a total of $2^L$ digital images can be uniquely identified. For example, for a 128-bit GUID having 6 fixed bits for the metadata part and 122 bits for the unique identifier, the covered range of images can be $2^{122}$ or $5.3 \times 10^{36}$.

Returning to FIG. 2, the image fingerprint module 116 further includes a key/data associator 206. The key/data associator 206 associates one or more images and/or non-image data with the key. The one or more images and/or non-image data with the key, in the illustrated example, are from the image database(s) 106 and/or the non-image data database(s) 108. The particular one or more images and/or non-image data associated with the key can be based on a default setting, a user preference, a user input, the key, the request to index the image, etc. The key/data associater 206 creates a key/value pair, which includes the key and a value to the associated data and/or the associated data.

The image finger printer module 116 further includes a key matcher 208. The key matcher 208 compares a key for a displayed bitmap digital image with the keys for bitmap digital images in the image database(s). In one instance, in which bitmap digital images in the image database(s) 106 have been previously indexed (i.e., fingerprinted), the key matcher 208 compares a key for an input bitmap digital image with the keys stored in the look up table database(s) 110. In another instance, in which bitmap digital images in the image database(s) 106 have not been previously indexed, the key matcher 208 compares a key for an input bitmap digital image with keys generated for bitmap digital images in the image database(s) 106 on the fly. In either instance, the key matcher 208 returns the key/value pair in response to an exact match.

The image finger printer module 116 further includes a data retriever 210. The data retriever 210 retrieves the associated data from the image database(s) 106 and/or the non-image data database (110) based on the retrieved link. The retrieved associated data is returned to the client 104.

Figure 6:
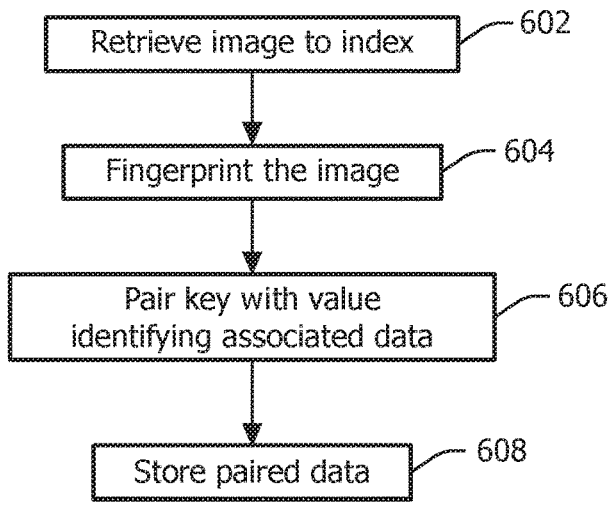
FIG. 6 illustrates an example method for fingerprinting an image and storing a key/value pair based thereon, creating an indexed database.

FIG. 6 illustrates an example method for fingerprinting an image and storing a key/value pair based thereon, creating an indexed database.

It is to be appreciated that the ordering of the acts is not limiting. As such, other orderings are contemplated herein. In addition, one or more acts may be omitted and/or one or more additional acts may be included.

At 602, an image to index is retrieved. As described herein, this can be in response to a request to fingerprint one or more images from the one or more image databases 106.

At 604, the image is fingerprinted, creating a unique key for the image. As described herein, the image can be fingerprinted as described in connection with FIG. 3 and/or otherwise.

At 606, the key is paired with associated data such as an image(s) from the image database(s) 106 and/or data from the associated database(s) 108.

At 608, the key/value pair is stored in the look-up database(s) 110.

If another image is to be fingerprinted, then acts 602-608 are repeated for the next image. Otherwise, the indexed database is ready to be employed.

Figure 7:
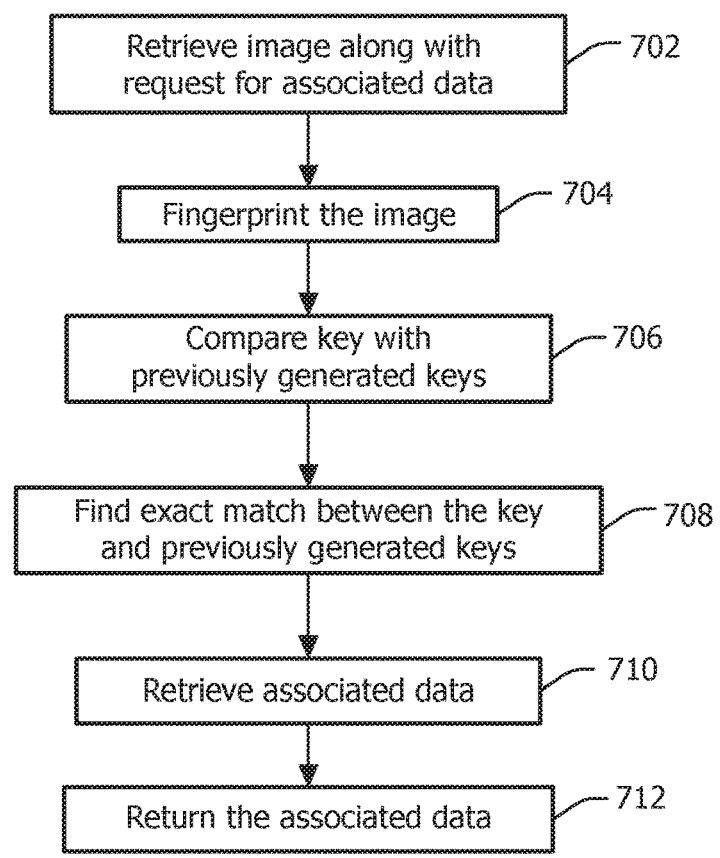
FIG. 7 illustrates an example method for employing the indexed database for images.

With this method, images are fingerprinted one-by-one or in parallel in advance using one or more fingerprinting schemes. If a new image is subsequently added to the one or more image database(s) 106, the finger printer module 116 can be executed again to update the look-up table database(s) 110. Alternatively, the ad-hoc approach described below can be used with the added image, FIG. 7 illustrates an example method of using an indexed database.

It is to be appreciated that the ordering of the acts is not limiting. As such, other orderings are contemplated herein. In addition, one or more acts may be omitted and/or one or more additional acts may be included.

At 702, an image is received along with a request for associated data from the client 104.

At 704, the image is fingerprinted, creating a unique key for the image. As described herein, the image can be fingerprinted as described in connection with FIG. 3 and/or otherwise.

At 706, the key is compared with the keys in the look-up database(s) 110.

At 708, in response to matching the key with a key in the look-up database(s) 110, the key/value pair is retrieved.

At 710, data identified by the value is retrieved.

At 712, the retrieved data is returned to the client 104.

An example leveraging an indexed database is described next.

The image finger printer module 116 can be installed on the client 104 with the legacy application. When an image of interest is rendered on the display of the legacy application, the image finger printer module 116 is executed to generate a key that is transmitted to the newer application. Alternatively, the image finger printer module 116 is installed on a different device and is launched on demand and/or automatically by a service based on predefined conditions.

With an indexed database, the image of interest was previously fingerprinted and the key is linked with associated data from the one or more associated database(s) 108, with the key/value pair stored in the look-up table database(s) 110. The newer application matches the newly generated key with the corresponding previously generated key and fetches the associated data. The fetched associated data is used by the newer application to manipulate the image, and the manipulated image may be displayed by the newer application and/or provided to the legacy application.

Figure 8:
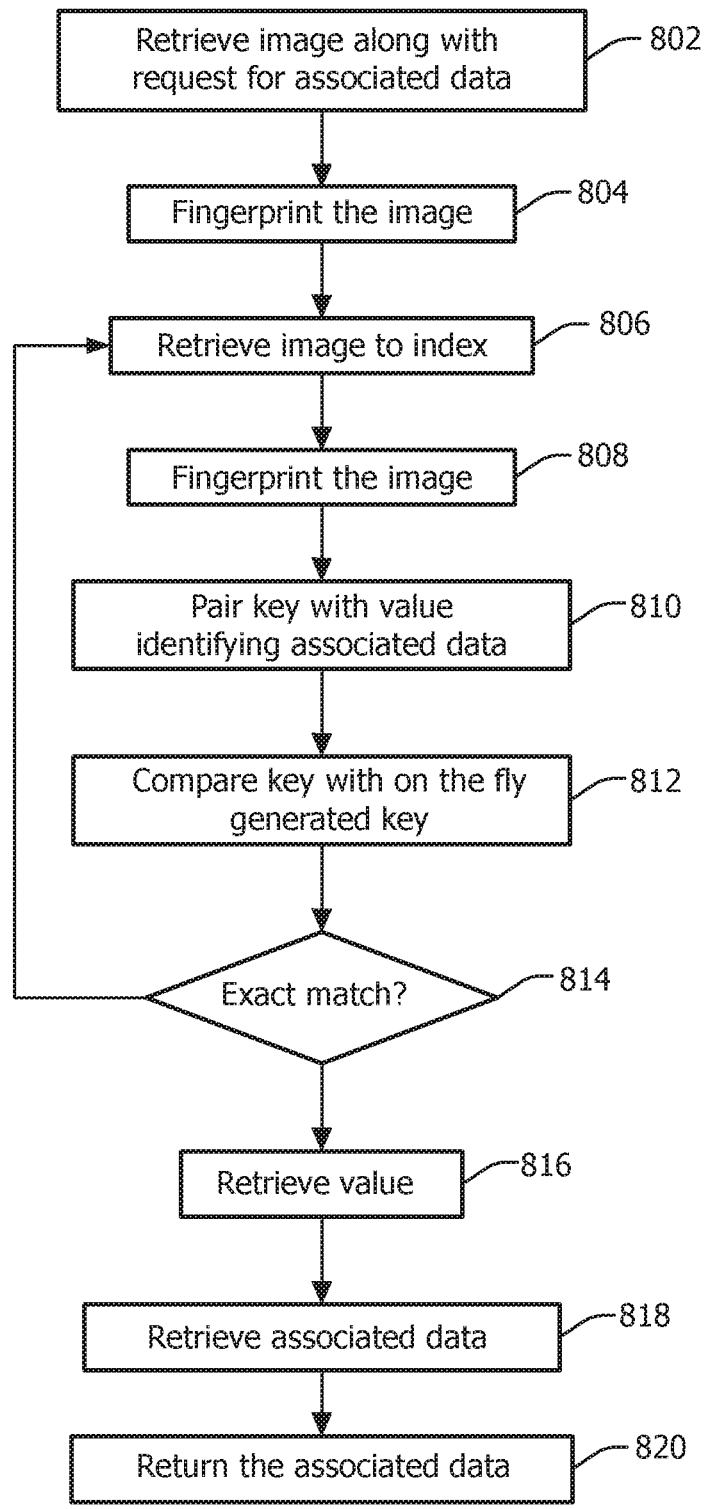
FIG. 8 illustrates an example method for employing a non-indexed database.

FIG. 8 illustrates an example method of using a non-indexed database.

It is to be appreciated that the ordering of the acts is not limiting. As such, other orderings are contemplated herein. In addition, one or more acts may be omitted and/or one or more additional acts may be included.

At 802, an image is received along with a request for associated data by the client 104.

At 804, the image is fingerprinted, creating a unique key for the image. As described herein, the image can be fingerprinted as described in connection with FIG. 3 and/or otherwise.

At 806, an image to index is retrieved from the one or more image databases 106.

At 808, the image is fingerprinted, creating a unique key for the image. The image is fingerprinted using the same scheme used in act 804.

At 810, the key is paired with a value.

At 812, the keys are compared.

At 814, it is determined if the keys are an exact match.

At 816, if the keys match, then the value is retrieved.

At 818, the associated data is retrieved based on the value.

At 820, the retrieved data is returned to the client 104.

If at 814 the keys do not match, then acts 806 to 814 are repeated for a different image from the one or more image databases 106.

The above approach represents an ad-hoc fingerprinting of each of the stored image one by one using the same fingerprinting scheme included in the database query. The request may include information that determines a set of image to fingerprint and an ordering of the fingerprinting. For example, the information may limit the fingerprinting to only spectral images, images created within a predetermined date ranger, images acquired based on an order from a particular clinician, etc.

An example application is described next. Similar to the above example, there are at least two incompatible applications, a "closed" legacy application that is used to view a radiology image with limited processing capabilities, and another more advanced application that offers more sophisticated processing capabilities. In this example, the input image on the legacy application is fingerprinted, and the key along with the sampling pattern identification is conveyed to the newer application.

The newer application invokes the computing system 102 to retrieve and return data associated with the image based on the key. The image finger printer module 116 iterates over its images in the one or more image database(s) 106, fingerprinting at least a sub-set of the image therein, until a match is found or all the relevant set of images is exhausted without finding a match. The matched image is then sent to the new application for further processing, and the manipulated image is conveyed to the legacy application.

Another example application for the ad-hoc fingerprinting technique is to find information about a given digital image assuming there is a database that associates addition information with digital images. Examples for the image in question could be: a digital photo of a painting taken by a visitor in an art exhibition; digital photo of an advertisement displayed on the streets taken by a random viewer, and/or a digital image found on the internet.

Similar to above, the input image is fingerprinted using one or more fingerprinting schemas. The fingerprint serves a database query for a dedicated service. The database iterates over its images and fingerprints them one by one using the provided fingerprinting scheme, until a match is found or all the relevant set of images is exhausted without finding a match. The information associated with the matched image is then sent to the querying application.

In a variation, the above methods are combined. For example, where there is no match with an indexed image and/or there are non-indexed images, the ad-hoc approach can be additionally used. Furthermore, the look-up table database(s) 110 can be updated and images are added to and/or removed from the image database(s) 106 and/or non-image data is added to and/or removed from the non-image data database(s) 108 and/or other associations between images and data are created.

The above methods may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
   receiving, from a client device, a digital image being visually observed and a first request, in electronic format, for electronically formatted first data associated with the digital image;
   generating a first key for the digital image, wherein the first key uniquely identifies the digital image;
   comparing the first key with at least one of previously or on the fly generated keys for images stored in an image database, wherein the previously or on the fly generated keys uniquely identify the images stored in the database;
   identifying a second key of the previously or on the fly generated keys that exactly matches the first key, within a predetermined tolerance;
   retrieving a first value paired with the second key, in response to the exact match;
   retrieving the first data associated with the digital image based on the first value; and
   returning, to the client device, the retrieved first data.

2. The method of claim 1, wherein the retrieved first data includes one or more of: a software application to process the digital image, an already processed version of the digital image, information to embed in the digital image being visually observed, or a history of an object or subject represented in the digital image.

3. The method of claim 1, further comprising:
   generating an on the fly key in response to at least one of not finding the exact match with any of the previously generated keys or an absence of any previously generated keys.

4. The method of claim 1, generating the second key on the fly, comprising:
   retrieving a stored digital image from the image database, wherein the stored image is a same image as the digital image;
   generating the second key for the retrieved stored digital image;
   associating the first data associated with the second key;
   comparing the first key with the second key; and
   determining the first and second keys match.

5. The method of claim 4, further comprising:
   applying a filter to reduce a number of images in the database to process.

6. The method of claim 5, wherein the filter extracts a sub-set of the images that have a predetermined characteristic.

7. The method of claim 5, wherein the filter applies a predetermined processing order.

8. The method of claim 1, generating the second key on the fly, comprising:
   retrieving a stored digital image from the image database, wherein the stored image is not a same image as the digital image;
   generating a third key for the retrieved stored digital image;
   associating second data associated with the third key;
   comparing the first key with the third key;
   determining the first and third keys do match;
   retrieving a next stored digital image from the image database, wherein the next stored image is a same image as the digital image;
   generating the second key for the retrieved stored digital image;
   associating the first data associated with the second key;
   comparing the first key with the second key; and
   determining the first and second keys match.

9. The method of claim 1, further comprising:
   receiving, from the client device, a second request, in electronic format, to at least one of create or update a key database;
   retrieving a first individual image from the image database;
   generating a fourth key for the first individual image, wherein the fourth key uniquely identifies the first individual image;
   associating third data associated with the retrieved first individual image;
   storing a key/value pair identifying the fourth key and the third data associated with the retrieved first individual image in the key database.

10. The method of claim 1, generating a key for the digital image, comprising:
sampling the digital image using a predetermined sampling pattern, in which the sampled data includes an electronic compressed representation of the digital image.

11. The method of claim 10, further comprising:
identifying the sampling pattern from a plurality of different sampling patterns based on one or more of an imaging modality that generated the digital image or an anatomical region represented in the digital image.

12. The method of claim 10, further comprising:
normalizing the digital image prior to sampling the digital image.

13. The method of claim 10, further comprising:
post-processing the samples.

14. The method of claim 10, further comprising:
packaging the samples into an electronic file, thereby creating the key.

15. A computing system, comprising:
a memory that stores instructions of an image finger printer module; and
a processor that receives a bitmap digital image and, with the image finger printer module, generates a first key, which is an electronic compressed representation of the bitmap digital image, that uniquely identifies the bitmap digital image, iteratively generates keys on the fly for images stored in an image database, compares the first key with a currently generated on the fly key until an exact match is found between the first key and on the fly generated key, retrieves data associated with the matched key, and returns the retrieved data to a requesting entity.

16. The computing system of claim 15, wherein the processor associates the first key with data, generates a key/value pair for the first key and the data; and stores the key/value in a searchable look-up table database.

17. The computing system of claim 16, wherein the processor samples the digital image using a predetermined sampling pattern and packages the samples into an electronic file, thereby creating the key.

18. The computing system of claim 17, wherein the processor generates on the fly keys in response to at least one of the processor not matching the first key with any previously generated keys or no previously generated keys.

19. The computing system of claim 15, wherein the processor compares the first key with previously generated keys for images stored in an image database until an exact match is found between the first key and a previously generated key, which is a second key; retrieves data associated with the second key, and returns the retrieved data to a requesting entity.

20. A computing system, comprising:
a memory that stores instructions of an image finger printer module; and
a processor that receives a bitmap digital image and generates a first key, which is an electronic compressed representation of the bitmap digital image, that uniquely identifies the bitmap digital image, associates the first key with data, generates a key/value pair for the first key and the data; and stores the key/value in a searchable look-up table database, samples the digital image using a predetermined sampling pattern and packages the samples into an electronic file, thereby creating the key, and generates on the fly keys in response to at least one of the processor not matching the first key with any previously generated keys or no previously generated keys.

21. The computing system of claim 20, wherein the processor compares the first key with previously generated keys for images stored in an image database until an exact match is found between the first key and a previously generated key, which is the second key; retrieves data associated with the second key, and returns the retrieved data to a requesting entity.

* * * * *